(12) United States Patent
Yoshimura

(10) Patent No.: US 11,497,471 B2
(45) Date of Patent: Nov. 15, 2022

(54) ULTRASONIC OBSERVATION DEVICE, ULTRASONIC DIAGNOSTIC SYSTEM, AND OPERATING METHOD OF ULTRASONIC OBSERVATION DEVICE

(71) Applicant: OLYMPUS CORPORATION, Tokyo (JP)

(72) Inventor: Takehiro Yoshimura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 293 days.

(21) Appl. No.: 16/405,349

(22) Filed: May 7, 2019

(65) Prior Publication Data
US 2019/0254631 A1    Aug. 22, 2019

Related U.S. Application Data

(63) Continuation of application No. PCT/JP2017/040103, filed on Nov. 7, 2017.

(30) Foreign Application Priority Data

Nov. 9, 2016  (JP) .............................. JP2016-219088

(51) Int. Cl.
*A61B 8/00* (2006.01)
*A61B 8/12* (2006.01)
*A61B 8/14* (2006.01)

(52) U.S. Cl.
CPC .............. *A61B 8/463* (2013.01); *A61B 8/12* (2013.01); *A61B 8/14* (2013.01); *A61B 8/462* (2013.01);
(Continued)

(58) Field of Classification Search
CPC .. A61B 8/463; A61B 8/12; A61B 8/14; A61B 8/462; A61B 8/465; A61B 8/4444; A61B 8/469; A61B 8/085; A61B 8/54
See application file for complete search history.

(56) References Cited

U.S. PATENT DOCUMENTS

2006/0241482 A1*  10/2006  Karasawa .............. A61B 8/488
                                                600/466
2009/0043195 A1*   2/2009  Poland .................. A61B 8/461
                                                600/437

(Continued)

FOREIGN PATENT DOCUMENTS

JP    2008136701 A    6/2008
JP    2010257328 A    11/2010
(Continued)

OTHER PUBLICATIONS

International Search Report dated Jan. 30, 2018 issued in PCT/JP2017/040103.

*Primary Examiner* — Christopher Koharski
*Assistant Examiner* — Taylor Deutsch
(74) *Attorney, Agent, or Firm* — Scully, Scott, Murphy & Presser, P.C.

(57) ABSTRACT

An ultrasonic observation device is disclosed that has an input device having a touch pad connected, and that displays on a display an ultrasound image generated based on an ultrasonic signal received from an ultrasound transducer that transmits an ultrasonic wave to an object to be observed and receives a reflected ultrasonic wave reflected by the object, the touch pad detecting a contact object that is brought in contact by an operator. The ultrasonic observation device includes a display controller that displays a rotation indicator that indicates a rotation direction when the ultrasound image is rotated about a predetermined rotation reference as a center, such that the rotation indicator is superimposed on the ultrasound image displayed on the display, according to a contact position of the contact object on the touch pad.

15 Claims, 13 Drawing Sheets

(52) U.S. Cl.
CPC ............ *A61B 8/465* (2013.01); *A61B 8/4444* (2013.01); *A61B 8/467* (2013.01)

(56) References Cited

U.S. PATENT DOCUMENTS

| | | | |
|---|---|---|---|
| 2010/0179427 A1* | 7/2010 | Yamamoto | A61B 8/469 600/443 |
| 2010/0271301 A1 | 10/2010 | Ohshita et al. | |
| 2010/0298701 A1 | 11/2010 | Shin | |
| 2014/0164965 A1* | 6/2014 | Lee | A61B 8/467 715/765 |
| 2018/0116633 A1* | 5/2018 | Hansen | A61B 8/54 |
| 2018/0271481 A1 | 9/2018 | Yoshimura | |

FOREIGN PATENT DOCUMENTS

| | | | |
|---|---|---|---|
| JP | 2010269139 A | 12/2010 | |
| JP | 2013116374 A | 6/2013 | |
| WO | 2017094421 A1 | 6/2017 | |

\* cited by examiner

ULTRASONIC OBSERVATION DEVICE, ULTRASONIC DIAGNOSTIC SYSTEM, AND OPERATING METHOD OF ULTRASONIC OBSERVATION DEVICE

CROSS-REFERENCE TO RELATED APPLICATION

This application is a continuation of PCT International Application No. PCT/JP2017/040103 filed on Nov. 7, 2017, which designates the United States, incorporated herein by reference, and which claims the benefit of priority from Japanese Patent Application No. 2016-219088, filed on Nov. 9, 2016, incorporated herein by reference.

BACKGROUND

The present disclosure relates to an ultrasonic observation device, an ultrasonic diagnostic system, and an operating method of an ultrasonic observation device.

To observe or inspect characteristics of a living tissue or a material that is an object to be observed, ultrasound images generated by using ultrasonic waves can be used. For diagnosis of a living tissue inside a body, ultrasound endoscopes in which an ultrasound transducer is provided at a distal end of an insertion portion are used.

In a diagnosis using an ultrasound endoscope, for example, an ultrasound image that is generated by an ultrasonic observation device based on ultrasound echoes acquired by the ultrasound endoscope is displayed on a display device. Settings of an observation mode and an observation condition at the diagnosis, an operation with respect to the ultrasound image, and the like are performed based on an instruction signal input through the input device.

As such an input device, an input device employing a touch pad has been proposed (for example, refer to Japanese Patent Laid-open Publication No. 2008-136701).

SUMMARY

The present disclosure is directed to an ultrasonic observation device, an ultrasonic diagnostic system, and an operating method of an ultrasonic observation device.

According to a first aspect of the present disclosure, there is provided an ultrasonic observation device to which an input device having a touch pad is connected, and that displays on a display an ultrasound image generated based on an ultrasonic signal received from an ultrasound transducer that transmits an ultrasonic wave to an object to be observed and receives a reflected ultrasonic wave reflected by the object, the touch pad detecting a contact object that is brought in contact by an operator. The ultrasonic observation device includes a display controller that displays a rotation indicator that indicates a rotation direction when the ultrasound image is rotated about a predetermined rotation reference as a center, such that the rotation indicator is superimposed on the ultrasound image displayed on the display, according to a contact position of the contact object on the touch pad.

According to a second aspect of the present disclosure, there is provided an ultrasonic diagnostic system including an ultrasonic observation device according to the first aspect; an ultrasound endoscope that has an ultrasound transducer transmits an ultrasonic wave to an object to be observed and receives a reflected ultrasonic wave reflected by the object, and that transmits an ultrasonic signal to the ultrasonic observation device; an input device that includes a touch pad, and that is connected to the ultrasonic observation device; and a display that displays an ultrasound image according to an output from the ultrasonic observation device.

According to a third aspect of the present disclosure, An operating method of an ultrasonic observation device to which an input device having a touch pad is connected, and that displays an ultrasound image generated based on an ultrasonic signal that is received from an ultrasound transducer that transmits an ultrasonic wave to an object to be observed and receives a reflected ultrasonic wave reflected by the object on a display. The method includes detecting a contact position on the touch pad by a display controller; displaying a rotation indicator that indicates a rotation direction when the ultrasound image is rotated about a predetermined rotation reference as a center, such that the rotation indicator is superimposed on the ultrasound image displayed on the display, according to the contact position.

According to a fourth aspect of the present disclosure, an ultrasonic observation device is provided which includes at least one processor comprising hardware, the at least one processor being configured to acquire an echo signal from an ultrasound endoscope; generate an ultrasound image data based on the echo signal; output the ultrasound image data to a display; receive contact position information from an input device having a touch pad, the contact position information indicating a contact position where a contact object is brought in contact with the touch pad; performing a coordinate conversion process in which first position coordinates in an operational area of the touch pad and second position coordinates in a display area of an ultrasound image displayed on the display are associated with each other; and display a rotation indicator indicating a rotational direction of the ultrasound image around a predetermined rotational center when a rotating operation is performed, such that the rotation indicator is superposed on the ultrasound image displayed on the display.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Hereinafter, embodiments of an ultrasonic observation device according to the present disclosure are described with reference to the accompanying drawings. The embodiments are not intended to limit the present disclosure. The present disclosure is applicable generally to ultrasonic observation devices to which an input device having a touch pad is connected.

Moreover, like reference symbols are given to like or corresponding components throughout the drawings. Furthermore, it is noted that the drawings are of schematic illustration, and a relationship in dimensions of respective components, a ratio of the respective components, and the like may differ from those in an actual situation. There can be part in which relationships in dimensions or ratios differ from one another among the drawings also.

Embodiment

Figure 1:
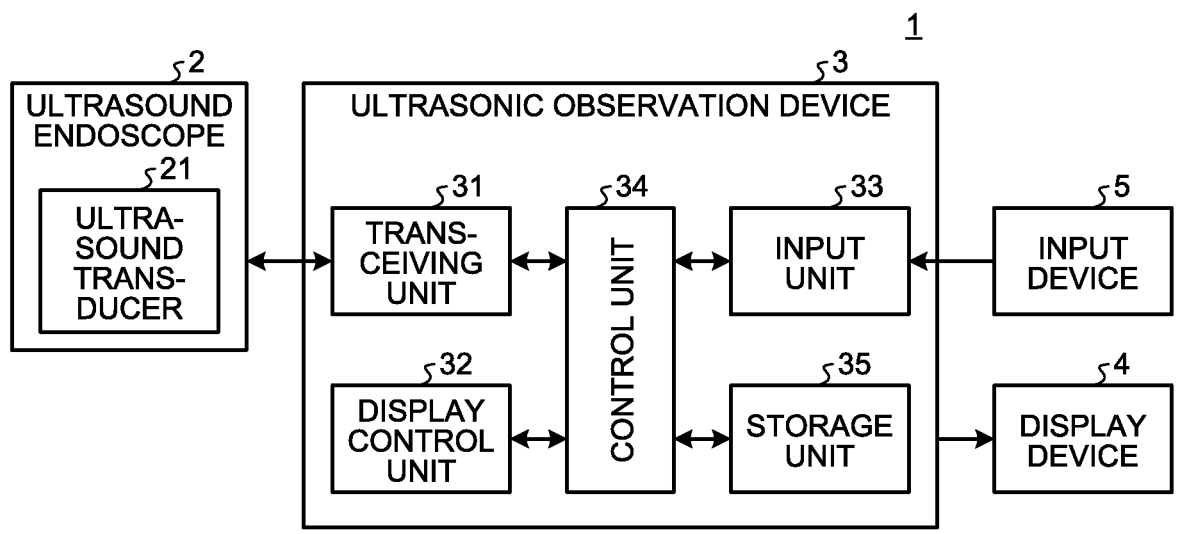
FIG. 1 is a block diagram illustrating a configuration of an ultrasonic diagnostic system that includes an ultrasonic observation device according to an embodiment of the present disclosure.

FIG. 1 is a block diagram illustrating a configuration of an ultrasonic diagnostic system that includes an ultrasonic observation device according to an embodiment of the present disclosure. As illustrated in FIG. 1, an ultrasonic diagnostic system 1 includes an ultrasound endoscope that transmits ultrasonic waves to a subject to be observed, and that receives ultrasonic waves reflected by the subject, an ultrasonic observation device 3 that generates an ultrasound image based on ultrasonic signal acquired by an ultrasound endoscope 2, a display device 4 that displays the ultrasound image generated by the ultrasonic observation device 3, and an input device 5 that accepts input of an instruction signal for observation mode setting, observation condition setting, or the like with respect to the ultrasonic observation device.

The ultrasound endoscope 2 has, at its distal end portion, an ultrasound transducer 21. The ultrasound transducer 21 converts an electrical pulse signal received from the ultrasonic observation device 3 into ultrasonic pulses (acoustic pulses) and irradiates the ultrasonic pulses to the subject. Then, the ultrasound transducer 21 receives ultrasonic echoes reflected by the subject, converts the received ultrasonic echoes into an electrical echo signal (ultrasonic wave signal) in which an ultrasonic echo is expressed by voltage variations, and outputs the electrical echo signal to the ultrasonic observation device 3. The ultrasound transducer 21 is realized by a radial transducer. The ultrasound endoscope 2 may cause the ultrasound transducer 21 to perform mechanical scanning, or to perform electronic scanning when the ultrasound transducer 21 is configured of multiple elements arranged in an array, and operates in such a manner that the multiple elements are electronically switched, or given delay time.

The ultrasound endoscope 2 usually includes an imaging device including an imaging optical system and an imaging element. The imaging device is inserted into a digestive canal (the esophagus, the stomach, the duodenum, the large intestine), or a respiratory organ (the trachea, the bronchus), thereby to capture an image of the digestive canal, the respiratory organ, and their peripheral organs (the pancreas, the gallbladder, the biliary duct, the biliary tract, a lymph node, a mediastinum organ, a blood vessel, and the like). Moreover, the ultrasound endoscope 2 includes a light guide that guides illumination light to be irradiated to the subject when capturing the image. A distal end portion of this light guide reaches a distal end of an insertion portion of the ultrasound endoscope 2 to be inserted to a subject, and a proximal end portion thereof is connected to a light source device that generates the illumination light.

The ultrasonic observation device 3 includes a transceiving unit 31, a display control unit 32, an input unit 33, a control unit 34, and a storage unit 35.

The transceiving unit 31 performs transmission and reception of an electrical signal with the imaging device and the ultrasound transducer 21. The transceiving unit 31 is electrically connected to the imaging device, and transmits imaging information about imaging timing and the like to the imaging device, and receives an imaging signal generated by the imaging device. Moreover, the transceiving unit 31 is electrically connected to the ultrasound transducer 21, and transmits an electrical pulse signal to the ultrasound transducer 21, and receives an echo signal that is an electrical reception signal from the ultrasound transducer 21. Specifically, the transceiving unit 31 generates an electrical pulse signal based on a predetermined waveform and transmission timing, and transmits the generated pulse signal to the ultrasound transducer 21.

The transceiving unit 31 performs sensitivity time control (STC) correction in which an echo signal having a larger reception depth is amplified at a higher amplification factor. The transceiving unit 31 subjects the amplified echo signal to filtering and the like, and then generates a digital high-frequency (radio frequency (RF)) signal of time domain to output.

The display control unit 32 generates endoscopic image data based on an imaging signal and ultrasound image data that corresponds to an electrical echo signal. Furthermore, the display control unit 32 superimposes various kinds of information on the endoscopic image data and the ultrasound image data to output, and controls display of the display device 4. The display control unit 32 is realized by using a central processing unit (CPU) having arithmetic and control functions, various kinds of arithmetic circuits, or the like.

The input unit 33 receives an instruction signal input by the input device 5, and accepts input of various kinds of information according to the received instruction signal. The various kinds of information include observation mode setting information, observation condition setting information (for example, a gain and switching of a display range, scroll specification information (a sliding direction and a sliding amount of a B-mode image)), rotation specification information (a rotation direction and a rotation amount of an ultrasound image), and the like.

The control unit 34 controls the entire ultrasonic diagnostic system 1. The control unit 34 is realized by using a CPU having arithmetic and control functions, various kinds of arithmetic circuits, and the like. The control unit 34 reads information stored in the storage unit 35 from the storage unit 35, and overall-controls the ultrasonic observation device 3 by performing various kinds of arithmetic processing related to an operating method of the ultrasonic observation device 3. Note that the control unit 34 may also be realized by the CPU or the like that constitutes the display control unit 32.

The storage unit 35 stores various kinds of programs to operate the ultrasonic diagnostic system 1, data including various kinds of parameters necessary for operation of the ultrasonic diagnostic system 1, and the like. The storage unit 35 stores, for example, an initial position (sound ray number) of a write start position (transmission start position of ultrasonic wave) of an ultrasound image.

Moreover, the storage unit 35 stores various kinds of programs including an operating program to perform an operating method of the ultrasonic diagnostic system 1. It is possible to distribute the operating program widely by storing the program in a computer-readable recording medium, such as a hard disk, a flash memory, a compact-disk read-only memory (CD-ROM), a digital versatile disk read-only memory (DVD-ROM), and a flexible disk. It is also possible to acquire the various kinds of programs described above by downloading through a communication network. The communication network herein is realized by, for example, an existing public line network, a local area network (LAN), a wide area network (WAN), or the like, and it does not matter whether the communication network is wired network or wireless network.

The storage unit 35 having the configuration as above is realized by using a read-only memory (ROM) in which various kinds of programs are installed in advance, a random access memory (RAM) in which arithmetic parameters and data of respective processing are stored, and the like.

The display device 4 is connected to the ultrasonic observation device 3. The display device 4 is configured with a display panel constituted of a liquid crystal display, an organic electroluminescence (EL) display, or the like. The display device 4 displays an ultrasound image output by the ultrasonic observation device 3, and various kinds of information relating to operation.

Figure 2:
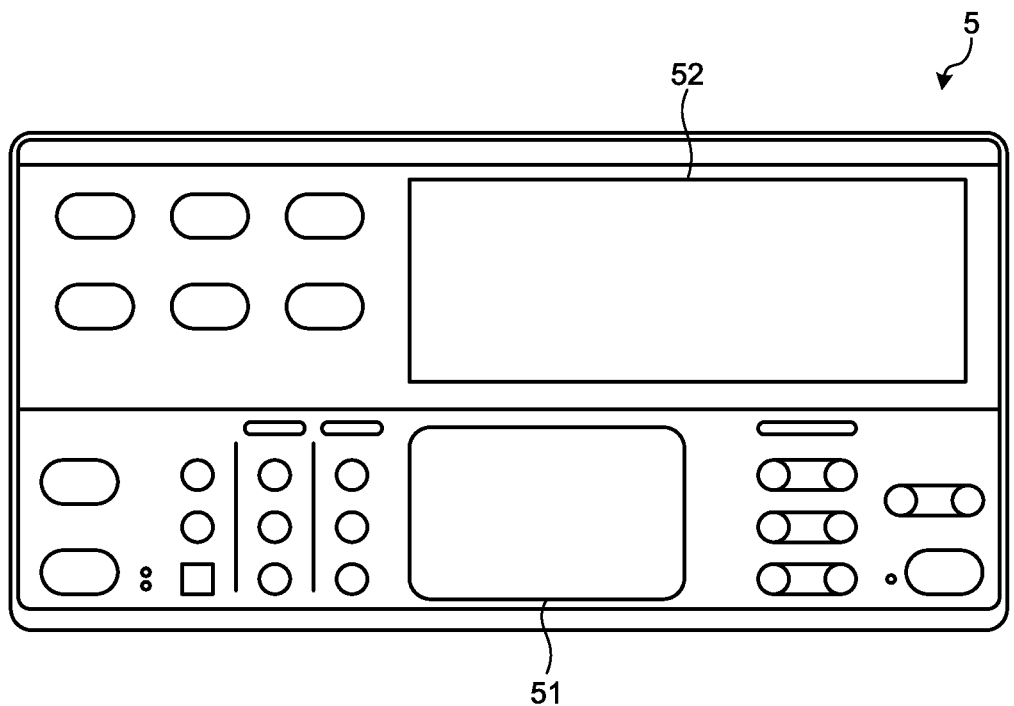
FIG. 2 illustrates a configuration of an input device illustrated in FIG. 1.

FIG. 2 illustrates a configuration of the input device illustrated in FIG. 1. As illustrated in FIG. 2, the input device 5 includes a casing as a main body, and a cover that covers an outer surface of the casing. The cover is made from silicone or the like, and thus the casing is kept in a watertight manner. The input device 5 includes within the casing a touch pad 51 that detects a contact of a finger of an operator or the like, and a display unit 52 that is capable of displaying various kinds of information. The input device 5 is electrically connected to the ultrasonic observation device 3 through a cable, and outputs a signal of instruction input from the touch pad 51 and the like to the input unit 33.

The input device 5 detects a contact position by a contact sensor when a contact object, such as a finger of an operator, contacts the touch pad 51, and outputs information on the contact position to the ultrasonic observation device 3. Moreover, when the contact object moves, keeping in contact with the touch pad 51, the input device 5 detects a moving direction and a moving amount, and outputs information on the moving direction and the moving amount to the ultrasonic observation device 3. The ultrasonic observation device 3 performs signal processing according to the contact position, the input moving direction and the moving amount of the contact position based on received information. Furthermore, the ultrasonic observation device 3 outputs, for example, an image for which a position of the image to be displayed on the display device 4 is slid or rotated based on the received information.

The display unit 52 displays information on the observation mode setting, the observation condition setting, and the like. The display unit 52 may be constituted of a touch panel, and configured to be able to change the observation mode setting, the observation condition setting, and the like.

Figure 3:
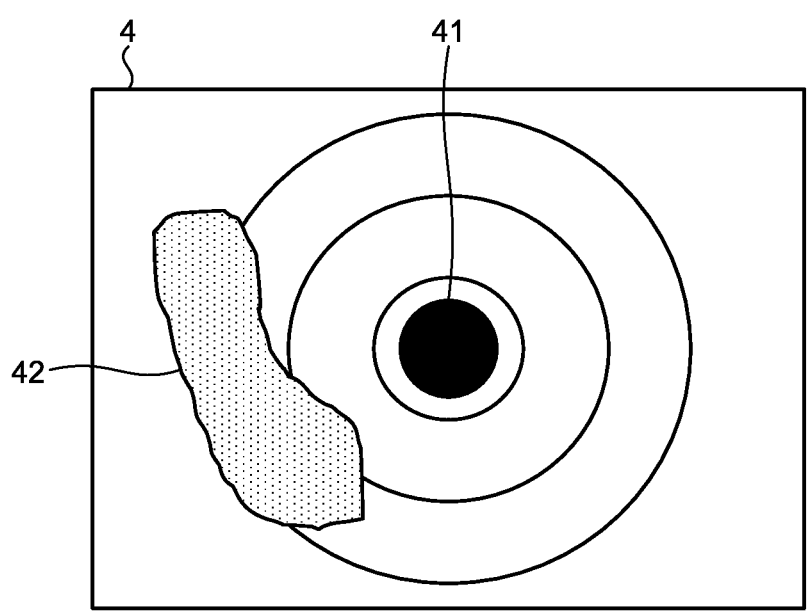
FIG. 3 illustrates an example of a screen displayed on a display device illustrated in FIG. 1.

Next, a rotation operation of an ultrasound image displayed on the display device 4 is described in detail. FIG. 3 illustrates an example of a screen displayed on a display device illustrated in FIG. 1. As illustrated in FIG. 3, an ultrasound image is displayed on the display device 4. In the ultrasound image, an ultrasound transducer region 41 that corresponds to the ultrasound transducer 21 and a tumor region 42 that shows a tumor are included.

Figure 4:
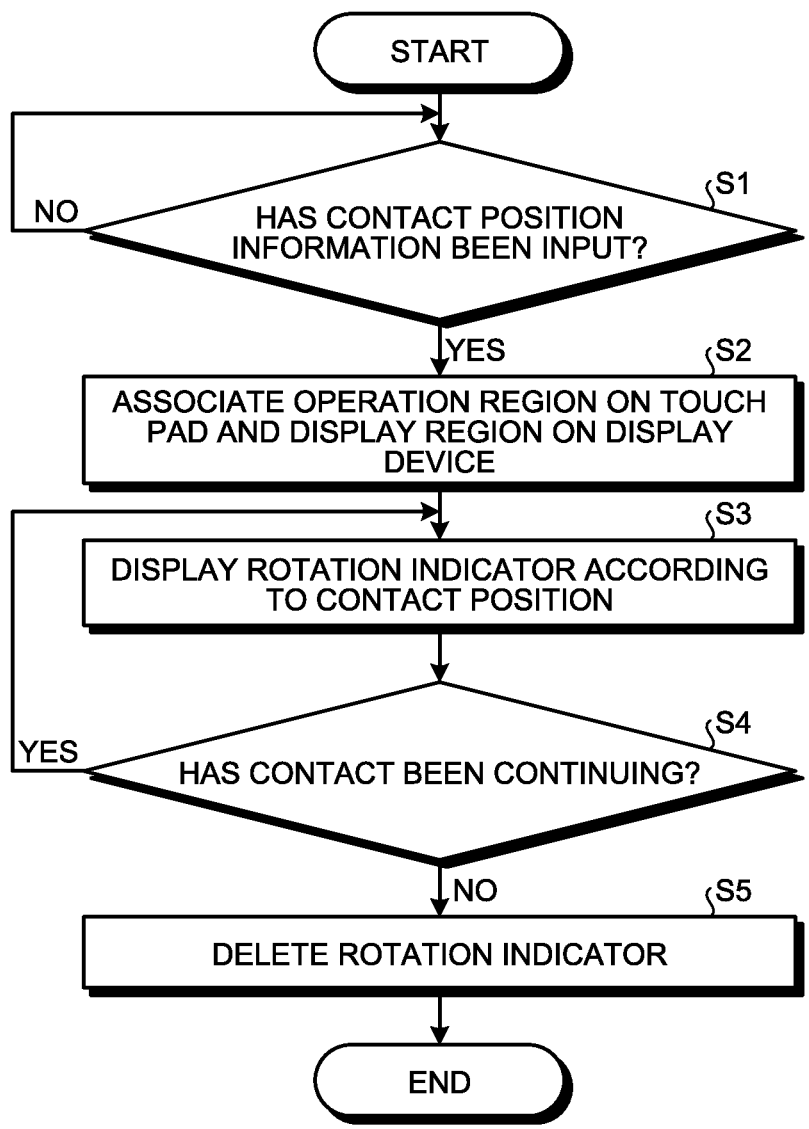
FIG. 4 is a flowchart illustrating an overview of processing performed by the ultrasonic diagnostic system according to the embodiment of the present disclosure.

An operator such as a doctor moves the tumor region 42 to a lower central part of the display device 4 to facilitate observation of the tumor. FIG. 4 is a flowchart illustrating an overview of processing performed by the ultrasonic diagnostic system according to the embodiment of the present disclosure. First, as illustrated in FIG. 4, the control unit 34 determines whether there has been an input of contact position information that is information indicating a position at which a finger of the operator or the like touches the touch pad 51, to the input unit 33 from the touch pad 51 (step S1).

When the control unit 34 determines that there has been no input of the contact position information (step S1: NO), the control unit 34 repeats step S1.

Figure 5:
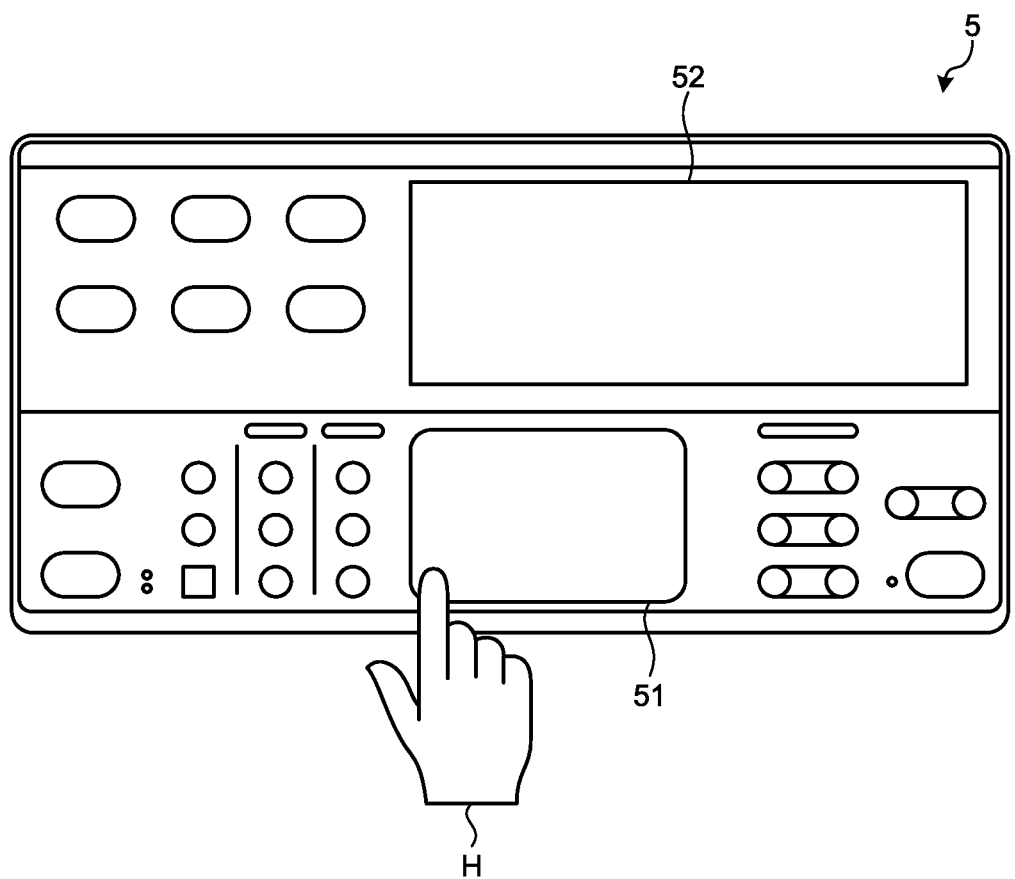
FIG. 5 illustrates input operated with respect to the input device illustrated in FIG. 2.

Suppose that a finger of the operator touches the touch pad 51. FIG. 5 illustrates input operated with respect to the input device illustrated in FIG. 2. As illustrated in FIG. 5, suppose that a hand H of the operator touches a left lower portion of the touch pad 51. At this time, the control unit 34 determines that there is an input of the contact position information (step S1: YES), and the control unit 34 associates an operation region on the touch pad 51 and a display region of the ultrasound image displayed on the display device 4 (step S2). At this time, the display control unit 32 detects a contact position of the finger of the operator with respect to the touch pad 51.

Figure 6:
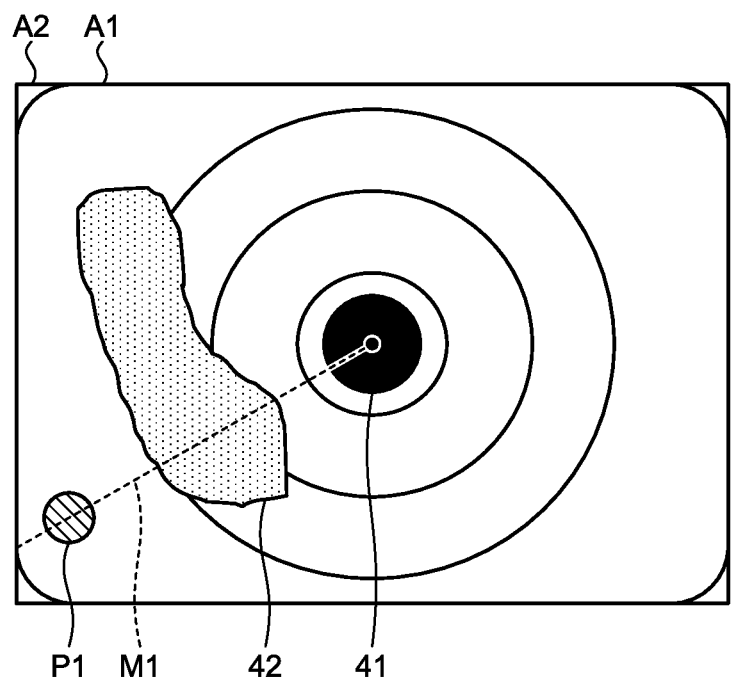
FIG. 6 is a diagram for explaining association of position coordinates of an operation region on a touch pad and position coordinates on an ultrasound image displayed on the display device.

FIG. 6 is a diagram for explaining association of position coordinates of an operation region on a touch pad and position coordinates on the ultrasound image displayed on the display device. As illustrated in FIG. 6, the display control unit 32 associates an operation region A1 and a display region A2 such that the sizes of the operation region A1 and the display region A2 are equal to each other when aspect ratios of the operation region A1 on the touch pad 51 and the display region A2 on the ultrasound image displayed on the display device 4 are the same. As described, the control unit 34 performs coordinate conversion such that position coordinates of an operation region on the touch pad 51 and position coordinates of a display region on an ultrasound image displayed on the display device 4 are associated with each other, to associate a position of a detected contact position on the touch pad 51 with a position of the display region on the ultrasound image displayed on the display device 4.

Subsequently, the display control unit 32 displays a rotation indicator to indicate a rotation direction for rotating operation of the ultrasound image about a center of the ultrasound transducer region 41 as a rotation center, which is a rotation reference, such that the rotation indicator is superimposed on the ultrasound image displayed on the display device 4 (step S3). The rotation indicator is an indicator to visualize a contact position of a contact object, such as a finger of the operator, on the display device 4. Viewing the rotation indicator, the operator can recognize how an image rotates in accordance with the rotating operation, regardless where the contact position of the finger of the operator is located on the touch pad 51.

Figure 7:
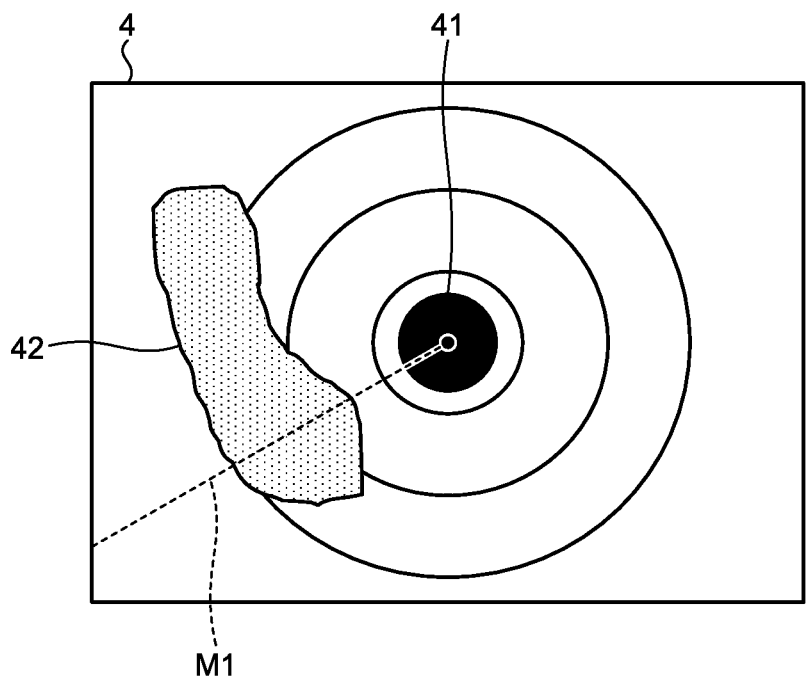
FIG. 7 illustrates a screen displayed on the display device when the input illustrated in FIG. 5 is performed.

Specifically, as illustrated in FIG. 6, the contact position of the finger of the operator on the touch pad 51 is a position P1, and the display control unit 32 superimposes, on the ultrasound image, a rotation indicator M1 that is a broken line extending from the center of the ultrasound transducer region 41 to the center of the position P1. FIG. 7 illustrates an image displayed on the display device when the finger of the operator touches the touch pad 51 as illustrated in FIG. 5. Referring to FIG. 7, the rotation indicator M1 is displayed on the display device 4. With this rotation indicator M1, the operator can visually recognize the contact position of the finger of the operator on the touch pad 51, and recognize how the image is rotated in accordance with how to move the finger.

Thereafter, the control unit 34 determines whether the contact state has been continuing (step S4). Specifically, the control unit 34 determines whether the input of the contact position information to the input unit 33 has been continuing.

Figure 8:
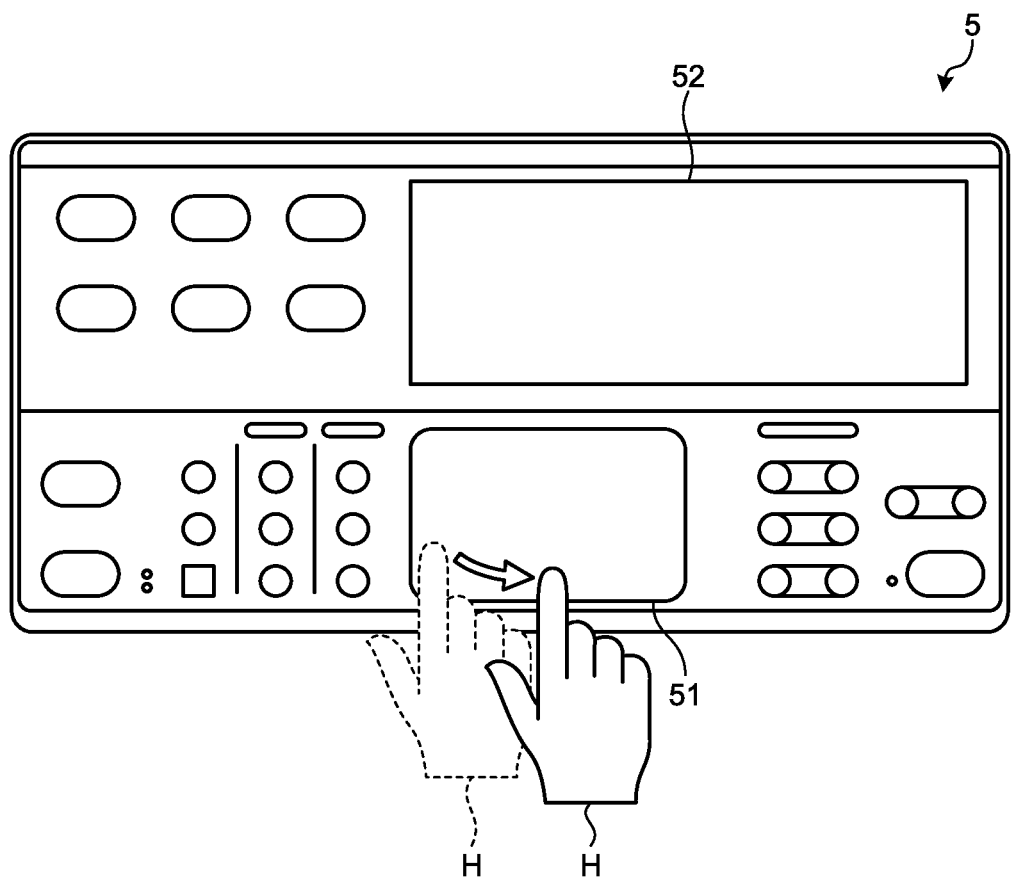
FIG. 8 illustrates input operated with respect to the input device illustrated in FIG. 1.

When the control unit 34 determines that the contact state has been continuing (step S4: YES), the processing returns to step S3, and the display control unit 32 keeps displaying the rotation indicator M1 on the display device 4 in a superimposing manner. Suppose that the operator has moved the finger and the contact position with respect to the touch pad 51 has moved. FIG. 8 illustrates that the finger of the operator moves on the touch pad 51 of the input device 5 illustrated in FIG. 1. As illustrated in FIG. 8, suppose that the hand H of the operator has moved, and the contact position has moved to a lower central portion of the touch pad 51. The display control unit 32 then displays the rotation indicator M1 toward a center of the contact position, which continuously moves, from the center of the ultrasound transducer region 41 in a superimposed manner.

Figure 9:
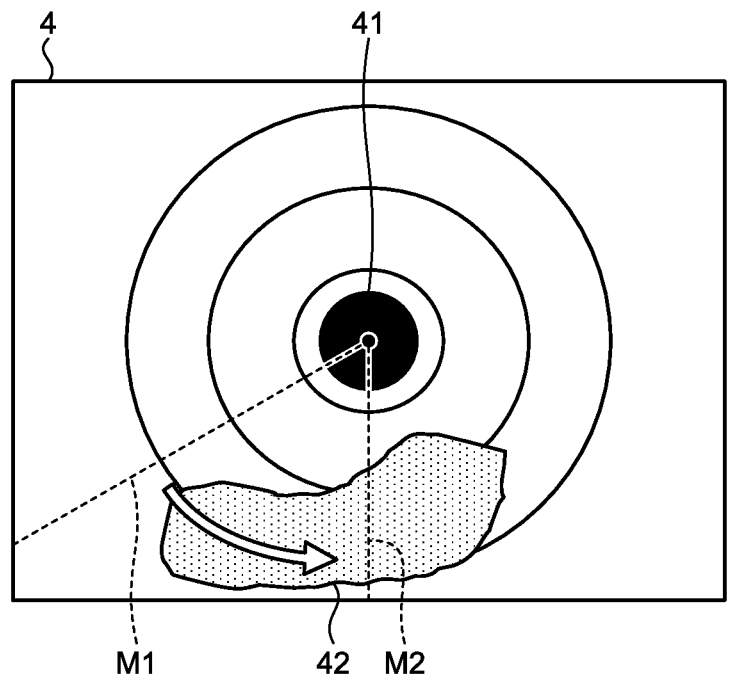
FIG. 9 illustrates a screen displayed on the display device when the input illustrated in FIG. 8 is performed.

FIG. 9 illustrates an image displayed on the display device when the hand H of the operator moves as illustrated in FIG. 8. As illustrated in FIG. 9, the rotation indication, which is once indicated by M1, moves to a position indicated by M2, along with the movement of the contact position. As described, because the rotation indicator moves, following an operation of the operator, the operator can rotate the ultrasound image displayed on the display device 4 to an intended direction. The operator can rotate the ultrasound image so that the tumor region 42 is positioned at the lower central portion of the display device 4.

Referring back to FIG. 4, at step S4, when the control unit 34 determines that the contact state has not been continuing (step S4: NO), the display control unit 32 deletes the rotation indicator M1 on the display device 4 (step S5), and a series of the processing is ended.

As described above, the ultrasonic observation device 3 enables an operator to visually recognize a contact position by the rotation indicator. Therefore, an ultrasonic observation device in which an intended operation can be performed without looking at the touch pad 51 is provided. Furthermore, in the ultrasonic observation device 3, an ultrasound image and a rotation indicator rotate according to movement of a contact position on the touch pad 51 and, therefore, an operator can perform rotating operation of the ultrasound image intuitively.

More specifically, in the ultrasonic observation device 3, because the operator can visually recognize the contact position by the rotation indicator, when the initial contact position of the finger is deviated, after redoing the contact to be at a correct position, rotation operation can be performed.

Moreover, in the ultrasonic observation device 3, when an initial contact position of a finger is shifted, by moving the finger such that an ultrasound image rotates in an intended rotation direction, rotation operation intended by the operator can be performed also. Specifically, for example, when the operator intends to rotate an ultrasound image in a counterclockwise direction by moving the finger from a lower left portion on the touch pad 51 to a lower central portion by moving a contact position of the finger toward a lower right direction, even when the initial contact position of the finger is deviated to be at an upper right portion, the operator visually recognizes the initial contact position of the finger by the rotation indicator, and moves the finger from the upper right portion to an upper central portion in an upper left direction, thereby being able to rotate the ultrasound image in the intended rotation direction (counterclockwise direction).

Figure 10:
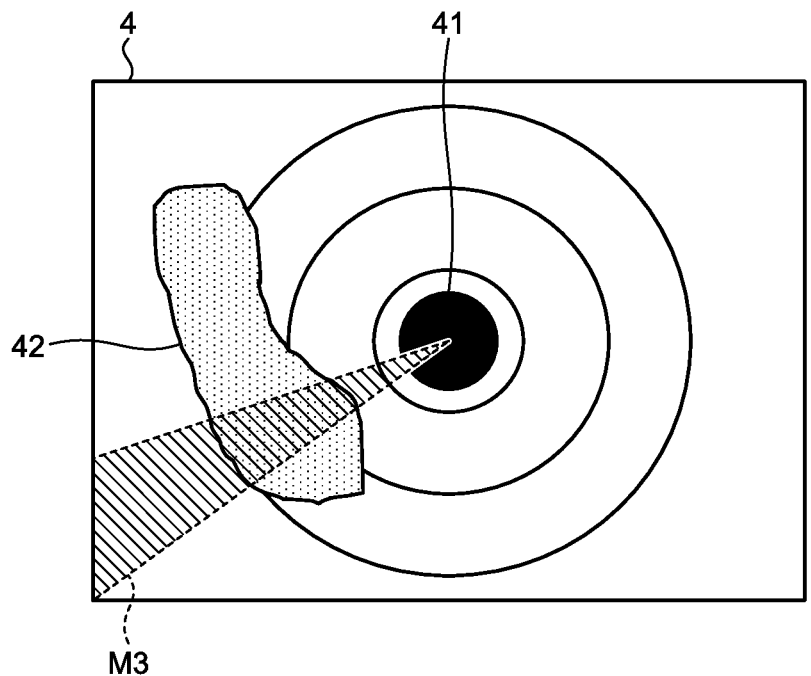
FIG. 10 illustrates another example of a rotation indicator.
Figure 11:
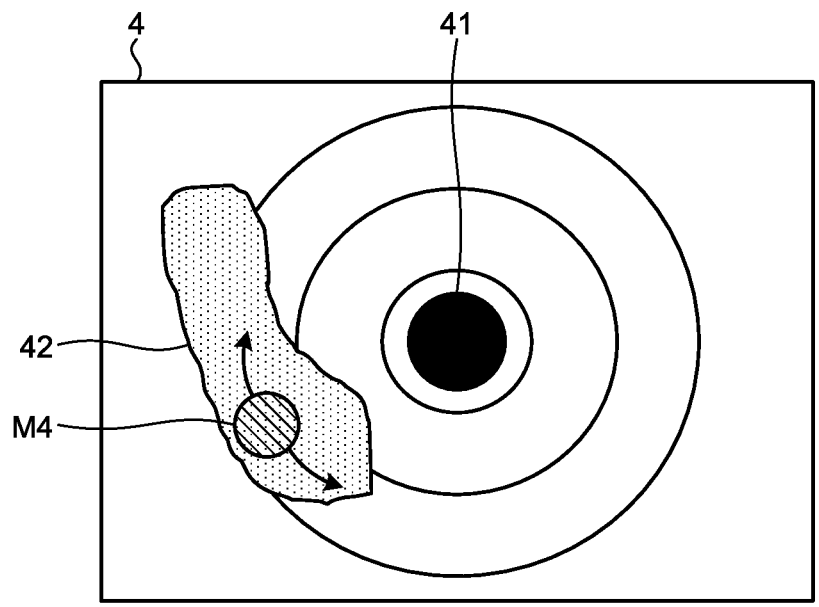
FIG. 11 illustrates another example of a rotation indicator.

The rotation indicator is not limited to be a straight line in a broken line or the like as explained above. FIG. 10 and FIG. 11 illustrate other examples of the rotation indicator. As illustrated in FIG. 10, the rotation indicator may be a rotation indication M3 that is a region extending from the center of the ultrasound transducer region 41 so as to include the contact region. As illustrated in FIG. 11, the rotation indicator may be a rotation indicator M4 that is a circle including the contact position and arrows indicating corresponding rotation directions. Furthermore, the rotation indicator may be configured not to be superimposed on an ultrasound image. For example, a contact-position display unit may be provided that displays a contact position with respect to the touch pad 51 with a rotation indicator, arranged next to an ultrasound image. In this case, the contact-position display unit in a shape corresponding to an operation region on the touch pad 51 may be displayed on the display device 4, and there is no need to acquire a correspondence between an operation region on the touch pad 51 and a display region on an ultrasound image displayed on the display device 4. As described, the configuration of the rotation indicator is not particularly limited, as long as it is configured to enable visual recognition of a contact position on the display device 4.

Moreover, in the embodiment described above, the rotation reference is taken as the center of the ultrasound transducer region 41, but it is not limited thereto. For example, the rotation reference may be a center of the display device 4, or may be set arbitrarily according to input by an operator.

Moreover, in the embodiment described above, the configuration in which the display control unit 32 deletes the rotation indicator at a point of time when a contact with respect to the touch pad 51 is ended has been described, but it is not limited thereto. The display control unit 32 may delete the rotation indicator displayed on an ultrasound image in a superimposed manner when predetermined time has passed since the contact with respect to the touch pad 51 starts, or when predetermined time has passed since the contact with respect to the touch pad 51 ends. Furthermore, the display control unit 32 may delete the rotation indicator when a contact position with respect to the touch pad 51 starts moving.

Moreover, in the embodiment described above, the associating method of an operation region and a display region when aspect ratios of an operation region of the touch pad 51 and a display region on an ultrasound image displayed on the display device are the same has been described, but other methods are described in the following. FIG. 12 to FIG. 19 are diagrams for explaining association of position coordinates in the operation region on the touch pad and position coordinates on an ultrasound image displayed on the display device.

Figure 12:
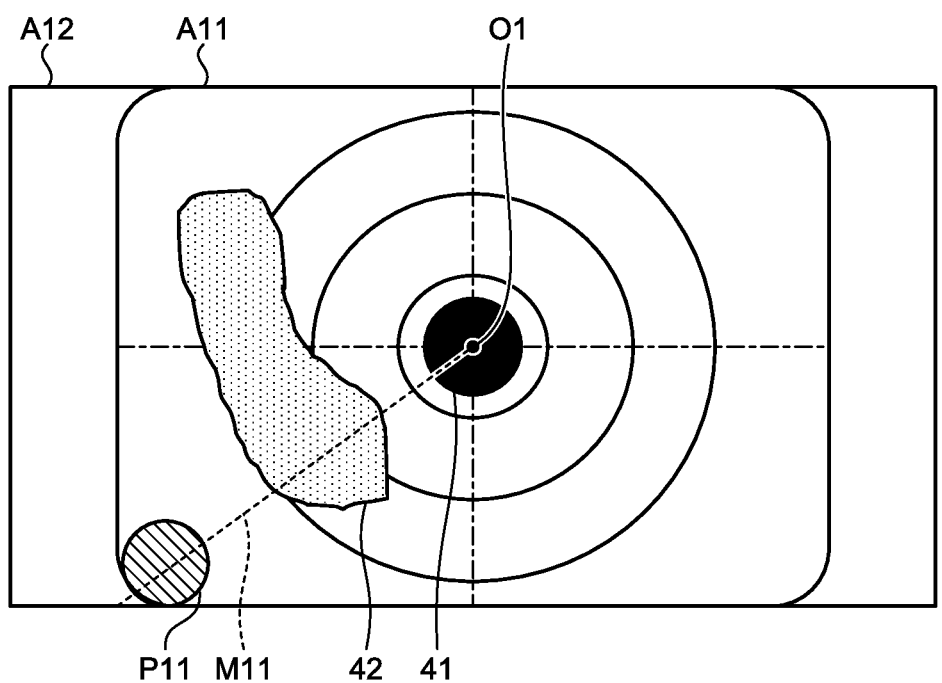
FIG. 12 is a diagram for explaining association of position coordinates in the operation region on the touch pad and position coordinates on an ultrasound image displayed on the display device.
Figure 13:
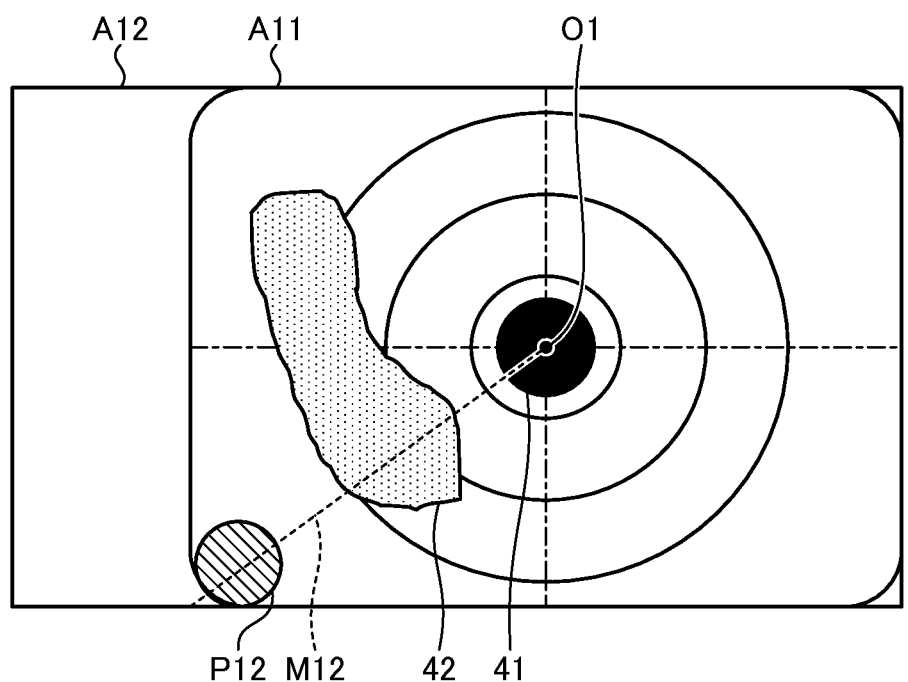
FIG. 13 is a diagram for explaining association of position coordinates in the operation region on the touch pad and position coordinates on an ultrasound image displayed on the display device.

As illustrated in FIG. 12, when an aspect ratio of an operation region A11 on the touch pad 51 and an aspect ratio of a display region A12 on an ultrasound image displayed on the display device 4 are compared, and when the display region A12 is larger in a horizontal direction, the regions are associated such that the operation region A11 is inscribed in the display region A12. At this time, the center of the ultrasound transducer region 41 displayed on the display device 4 coincides with a center O1 (intersection point of alternate long and short dashed lines in the drawing) of the operation region A11. That is, as illustrated in FIG. 12, when the center of the ultrasound transducer region 41 is positioned at the center of the display device 4, the center O1 of the operation region A11 is positioned at the center of the display device 4. On the other hand, as illustrated in FIG. 13, when the center of the ultrasound transducer region 41 is deviated from the center of the display device 4, the center O1 of the operation region A11 is positioned at the center of the ultrasound transducer region 41 displayed on the display device 4. As described, the display control unit 32 performs coordinate conversion such that position coordinates in the operation region on the touch pad 51 and position coordinates in the display region on the ultrasound image are associated with each other. The display control unit 32 displays, when a contact position by an operator is a position P11 or a position P12, a rotation indicator M11 or a rotation indicator M12 superimposing thereon on the display device 4. As a result, in the ultrasonic observation device 3, the operator can visually recognize the contact position by the rotation indicator and, therefore, can perform an intended operation without looking at the touch pad 51.

Figure 14:
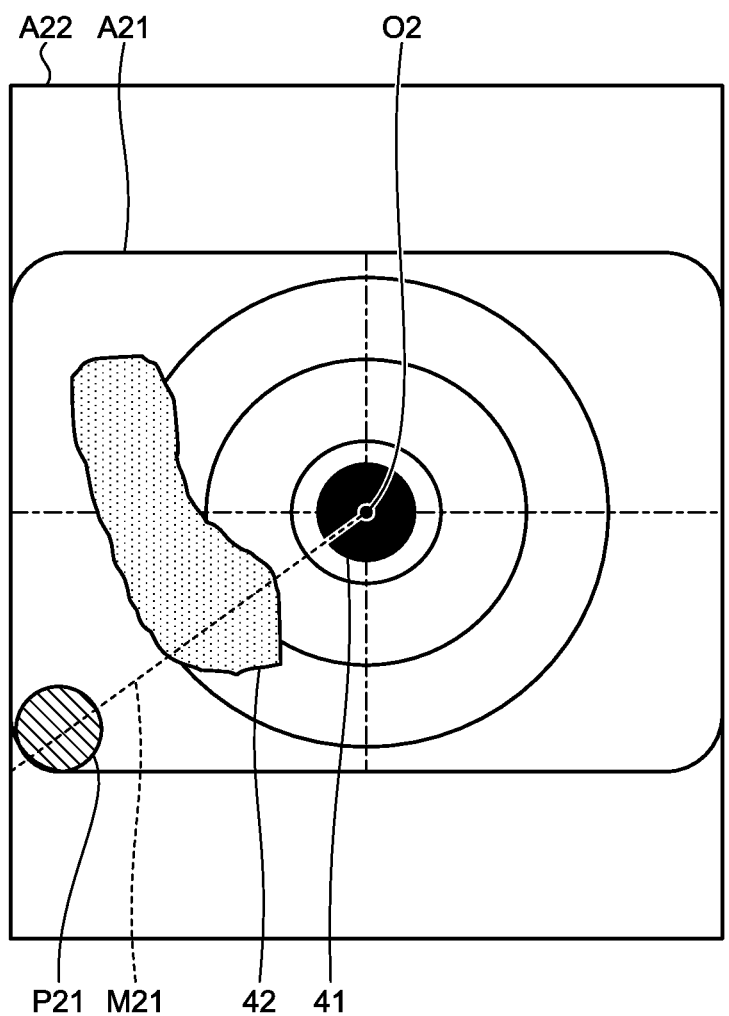
FIG. 14 is a diagram for explaining association of position coordinates in the operation region on the touch pad and position coordinates on an ultrasound image displayed on the display device.
Figure 15:
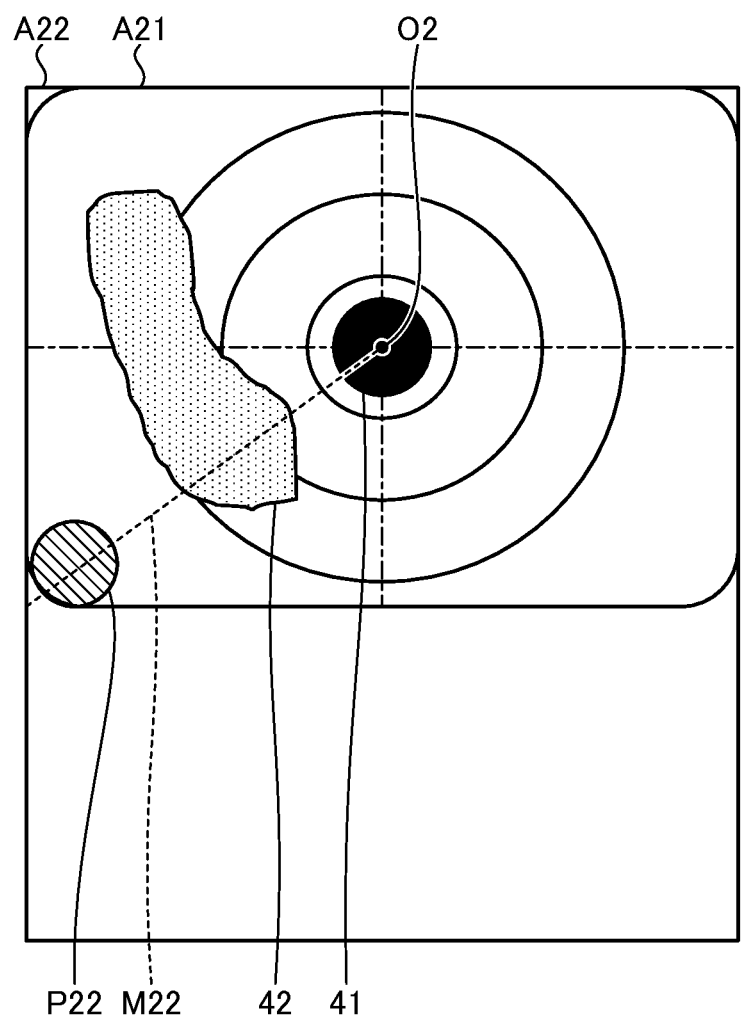
FIG. 15 is a diagram for explaining association of position coordinates in the operation region on the touch pad and position coordinates on an ultrasound image displayed on the display device.

As illustrated in FIG. 14, when an aspect ratio of an operation region A21 on the touch pad 51 and an aspect ratio of a display region A22 on an ultrasound image displayed on the display device 4 are compared, and when the display region A22 is larger in a vertical direction, the regions are associated such that the operation region A21 is inscribed in the display region A22. At this time, the center of the ultrasound transducer region 41 displayed on the display device 4 coincides with a center O2 of the operation region A21. That is, as illustrated in FIG. 14, when the center of the ultrasound transducer region 41 is positioned at the center of the display device 4, the center O2 of the operation region A21 is positioned at the center of the display device 4. On the other hand, as illustrated in FIG. 15, when the center of the ultrasound transducer region 41 is deviated from the center of the display device 4, the center O2 of the operation region A21 is positioned at the center of the ultrasound transducer region 41 displayed on the display device 4. As described, the display control unit 32 performs coordinate conversion such that position coordinates in the operation region on the touch pad 51 and position coordinates in the display region on the ultrasound image displayed on the display device 4 are associated with each other. The display control unit 32 displays, when a contact position by an operator is a position P21 or a position P22, a rotation indicator M21 or a rotation indicator M22 superimposing thereon on the display device 4. As a result, in the ultrasonic observation device 3, the operator can visually recognize the contact position by the rotation indicator and, therefore, can perform an intended operation without looking at the touch pad 51.

Figure 16:
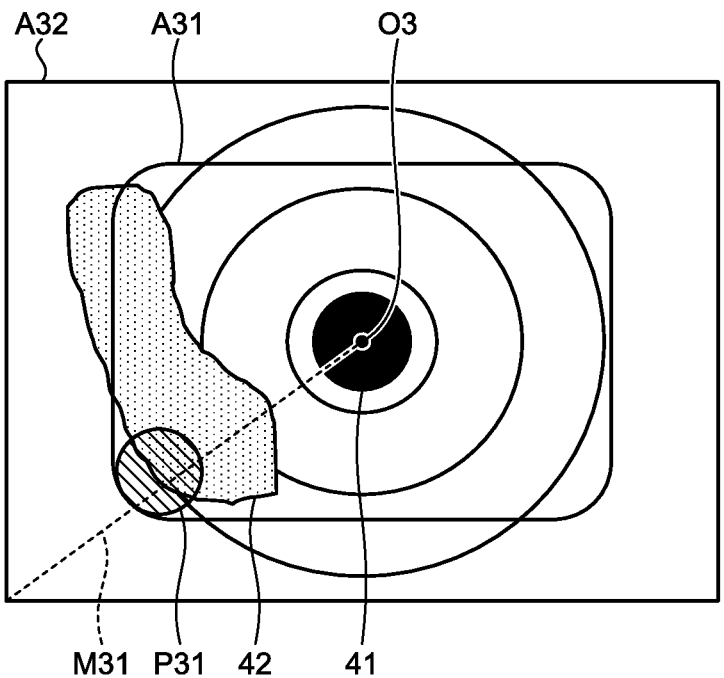
FIG. 16 is a diagram for explaining association of position coordinates in the operation region on the touch pad and position coordinates on an ultrasound image displayed on the display device.

As illustrated in FIG. 16, the regions may be associated such that an operation region A31 on the touch pad 51 is included in a display region A32 on an ultrasound image displayed on the display device 4. At this time, the center of the ultrasound transducer region 41 displayed on the display device 4 coincides with a center O3 of the operation region A31. As described, the display control unit 32 performs coordinate conversion such that position coordinates in the operation region on the touch pad 51 and position coordinates in the display region on the ultrasound image displayed on the display device 4 are associated with each other. The display control unit 32 displays, when a contact position by an operator is a position P31, a rotation indicator M31 superimposing thereon on the display device 4. As a result, in the ultrasonic observation device 3, the operator can visually recognize the contact position by the rotation indicator and, therefore, can perform an intended operation without looking at the touch pad 51.

Figure 17:
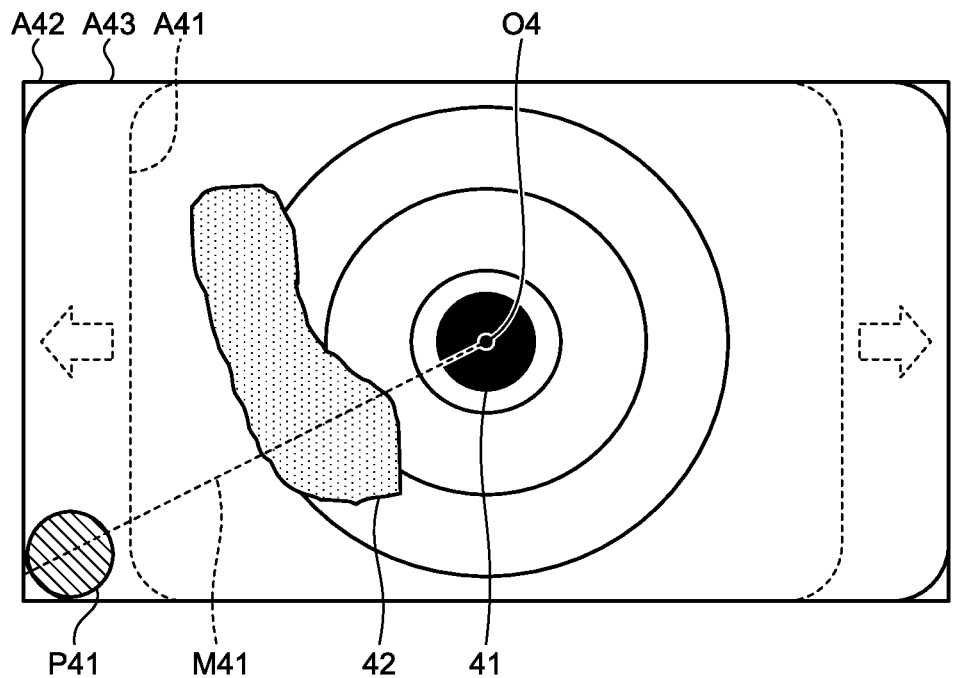
FIG. 17 is a diagram for explaining association of position coordinates in the operation region on the touch pad and position coordinates on an ultrasound image displayed on the display device.

As illustrated in FIG. 17, an operation region A41 on the touch pad 51 may be converted into a region A43 that is expanded in a left and right direction so as to correspond with a display region A42 on an ultrasound image displayed on the display device 4. At this time, the center of the ultrasound transducer region 41 displayed on the display device 4 coincides with a center O4 of the operation region A41. As described, the display control unit 32 performs coordinate conversion such that position coordinates in the operation region on the touch pad 51 and position coordinates in the display region on the ultrasound image displayed on the display device 4 are associated with each other. The display control unit 32 displays, when a contact position by an operator is a position P41, a rotation indication M41 superimposing thereon on the display device 4. As a result, in the ultrasonic observation device 3, the operator can visually recognize the contact position by the rotation indicator and, therefore, can perform an intended operation without looking at the touch pad 51. Similarly, an operation region on the touch pad 51 may be converted into a region expanded in a vertical direction so as to correspond with a display region on an ultrasound image displayed on the display device 4.

Figure 18:
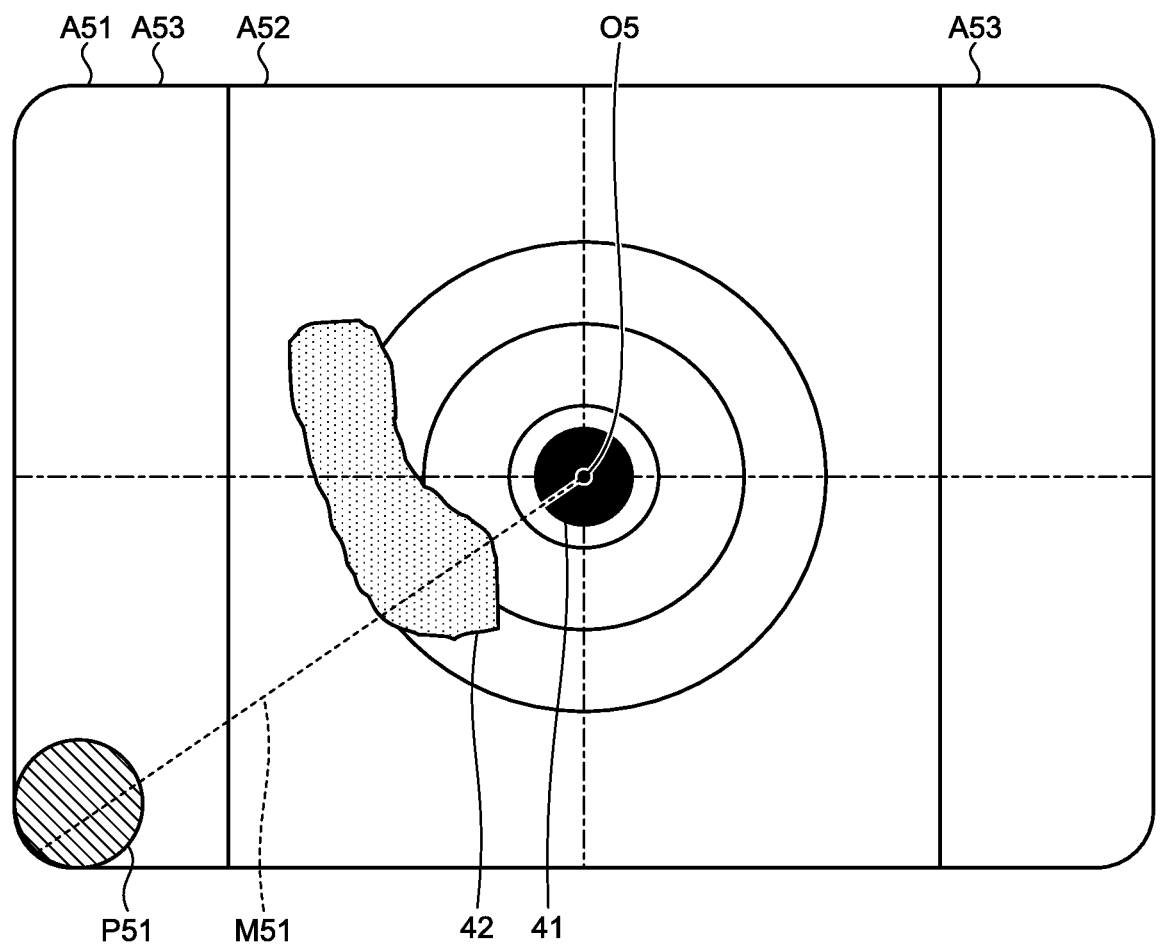
FIG. 18 is a diagram for explaining association of position coordinates in the operation region on the touch pad and position coordinates on an ultrasound image displayed on the display device.
Figure 19:
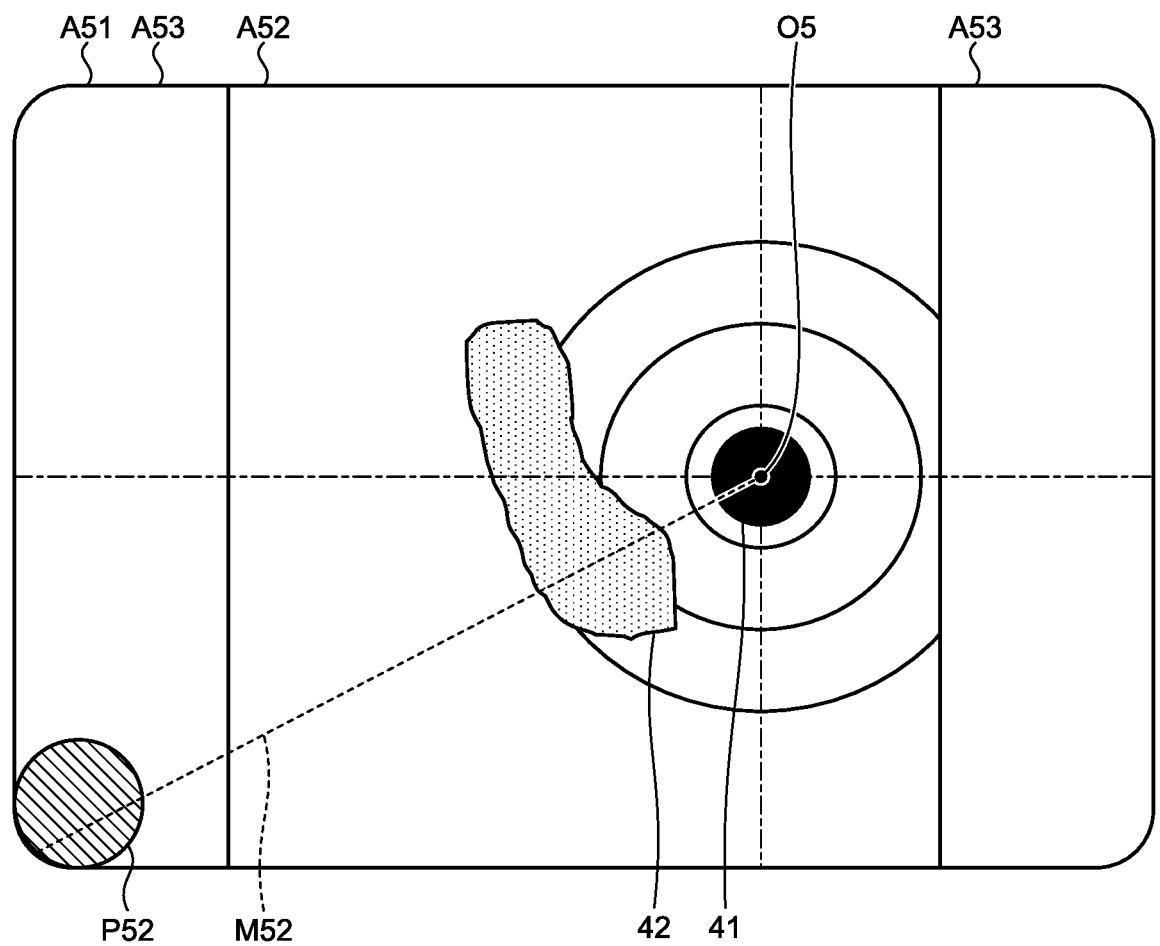
FIG. 19 is a diagram for explaining association of position coordinates in the operation region on the touch pad and position coordinates on an ultrasound image displayed on the display device.

As illustrated in FIG. 18, a display region A52 on an ultrasound image displayed on the display device 4 may be associated with an operation region A51 on the touch pad 51 so as to be included in the operation region A51 on the touch pad 51. On both left and right sides of the display region A52, virtual display regions A53 that correspond to differences between the operation region A51 and the display region A52 may be set. That is, regions which are present in the operation region A51 but not in the display region A52 are complemented by the virtual display regions A53. At this time, the center of the ultrasound transducer region 41 displayed on the display device 4 coincides with a center O5 of the operation region A51. That is, as illustrated in FIG. 18, when the center of the ultrasound transducer region 41 is positioned at the center of the display device 4, the center O5 of the operation region A51 is positioned at the center of the display device 4. On the other hand, as illustrated in FIG. 19, when the center of the ultrasound transducer region 41 is deviated from the center of the display device 4, the center O5 of the operation region A51 is positioned at the center of the ultrasound transducer region 41 displayed on the display device 4. The display control unit 32 displays, when a contact position by an operator is a position P51 or a position P52 in the virtual display region A53, a rotation indicator M51 or a rotation indicator M52 that extends from the center of the ultrasound transducer region 41 to the position P51 or the position P52, respectively, superimposing thereon on the display device 4. As a result, in the ultrasonic observation device 3, the operator can visually recognize the contact position by the rotation indicator and, therefore, can perform an intended operation without looking at the touch pad 51. Note that it suffices that the virtual display regions are positioned in an outer periphery of the display region A52, and thus the virtual display regions may be arranged above or below the displayer region A52.

Moreover, the ultrasonic diagnostic system 1 may have functions as described in the following.

When the ultrasound endoscope 2 is a radial scope having the radial ultrasound transducer 21, the display control unit 32 may display an UP position indicator to indicate an upward direction of the ultrasound transducer 21 in part of the ultrasound transducer region 41 displayed on the display device 4 in a superimposed manner. By displaying the UP position indicator, an operator can be aware of the upward direction of the radial ultrasound transducer 21 even when an ultrasound image is rotated, and can grasp a turning direction when a distal end of an insertion portion is operated to be bent.

The display control unit 32 may display assignments of buttons (buttons to perform freeze, release, and the like) of an operation unit of the ultrasound endoscope 2 at ultrasonic diagnosis using the ultrasound endoscope 2. By displaying the assignments, the operator can be aware of what kind of operation is performed when which button is pressed. Furthermore, the display control unit 32 may have a function of switching between a mode in which the assignments of the buttons are displayed all the time at ultrasonic diagnosis and a mode in which the assignments are displayed for predetermined time only when operation with respect to a button of the operation unit is performed, and then deleted.

The storage unit 35 may store a date and a time of storing an image such as an ultrasound image, when storing the image. Furthermore, the display control unit 32 displays indicators (mark, underline, frame, and the like) superimposing on a display of the date in the display device 4 at the time of reproducing a stored image, when a date of storage and a date of reproduction are different.

The display control unit 32 deletes information not relating to reproduction, when reproducing a stored image, and displays an operation panel (play, double speed, fast forward, rewind, stope, pause, and the like) relating to reproduction in the region.

The control unit 34 may have a function of searching for a stored image stored in the storage unit 35. The search function may include a function enabling to select from types, names, dates of storage, and the like of data. Furthermore, the display control unit 32 may have a function of displaying stored images stored in the storage unit 35, sorted based on types, names, dates of storage, and the like of data.

On the display unit 52, a sensitive time control (STC) adjustment lever can be displayed. In the STC adjustment lever, for example, a horizontal axis corresponds to depth, and a vertical axis corresponds to brightness. When the operator runs his/her finger along the display unit 52, which is a touch panel, it is possible to adjust to STC according to a moving path of the finger.

On the display unit 52 of input device 5, a keyboard can be displayed only when needed by performing a predetermined operation. With the keyboard, characters can be input through the display unit 52 that is a touch panel. Furthermore, the input characters are displayed on the display unit 52. When characters are input by the keyboard on the display unit 52, candidate words are narrowed down from among medical terms that have been registered in advance in the system, and each of the candidate words is displayed on the touch panel in a form of buttons (annotation function). By pressing the button, an intended word can be input. Furthermore, a function of switching the order of the candidate words according to a past input frequency may be included.

The display control unit 32 may have a function of switching between a mode in which an ultrasound image is slid in the same direction as an operation direction on the touch pad 51 and a mode in which an ultrasound image is slid in an opposite direction to an operation direction on the touch pad 51. As a result, the operator can move an ultrasound image by sliding in either mode easier to operate. A function of switching between a mode in which an ultrasound image is rotated in the same direction as an operation direction on the touch pad 51 and a mode in which an ultrasound image is rotated in an opposite direction to an operation direction on the touch pad 51 when an ultrasound image is rotated may be included.

The display control unit 32 may have a function of flipping an ultrasound image vertically when a convex ultrasound endoscope is used. Moreover, the display control unit 32 may be configured to be able to enable or disable vertical flipping per probe.

The display control unit 32 may have a function of zooming in on an ultrasound image to an arbitrary depth according to an operation with respect to the touch pad 51 (zoom function). The display control unit 32 automatically focuses according to a size of a range to be zoomed at zooming. Furthermore, the display control unit 32 may display a scale bar, superimposing on the ultrasound image. The display control unit 32 may change the scale of the scale bar in accordance with zooming.

The display control unit 32 may display a zoom box to flexibly select a region to be zoomed, superimposing on an ultrasound image. The zoom box can be slid and moved according to an operation with respect to the touch pad 51. By bringing the zoom box to a desirable position to be zoomed, and then double tapping the touch pad 51, the region is zoomed. Furthermore, by performing a pinching in or pinching out operation on the touch pad 51 in this state, a zoom magnification can be changed. Moreover, by performing a slide operation in a zoomed-in state, the zoom is released while the slide operation is being performed, and after the slide operation is ended, a zoomed-in image of the position is displayed. Thereafter, by double tapping the touch pad 51, the zoom is released.

The display control unit 32 may have a function of performing a noise rejection processing to cut noises.

The control unit 34 may have a function of adjusting sensitivity to an operation input to the touch pad 51 individually through the input unit 33 according to a mode.

The input device 5 may have a function of switching on and off of light, or colors of light according to the state of a button so that the state of the button can be easily recognized. Specifically, when a button is selected, the button is lit in green or blue. When the button is not selected but is selectable, the button is lit in white, and when the button is not selectable, the button is not lit.

In the input device 5, assignment of buttons may be changed according to a mode. Furthermore, when the display unit 52 is a touch panel, assignment of buttons displayed on the display unit 52 may be changed according to a mode. In this case, functions assigned to the buttons are displayed superimposing on the buttons displayed on the display unit 52. Furthermore, in the input device 5, assignment of the touch pad 51 may be changed according to a mode. In this case, a function assigned to the touch pad 51 is displayed on the display unit 52.

The control unit 34 reads recommended settings from the storage unit 35 according to identification (ID) of the ultrasound endoscope 2. Furthermore, the settings according to the ID can be edited, and stored in the storage unit 35. In this case, to make it clear which recommended setting is edited by the operator, an identifier according to an ID of the ultrasound endoscope 2 is determined. Furthermore, the setting can be separately set per district in which the ultrasound endoscope 2 is used. Similarly, a series name of the ultrasound endoscope 2 can be set per district in which the ultrasound endoscope 2 is used.

The control unit 34 may have a function of detecting the ID of the connected ultrasound endoscope 2, and of reading an ID of the same ultrasound endoscope used at a previous time and settings of the same identifier automatically from the storage unit 35. Furthermore, when reading the settings from the storage unit 35, settings related to the ID of the ultrasound endoscope 2 can be displayed on the display device 4 on a priority basis.

When the settings are saved in the storage unit 35 during inspection, it is possible to select settings of a mode employed right before saving or settings of all modes, as setting to be saved. Among settings that can be set by an operator, setting that is saved during an inspection and setting that is not saved are distinguished. Moreover, as for a name of the setting to be saved at the time of saving setting, the ID and the identifier of the ultrasound endoscope 2 are automatically given. Additionally, a desirable name can be added following the ID and the identifier by the operator.

When settings are edited, settings are classified per observed part (digestive canal, bronchus, and the like), and the connected ultrasound endoscope 2 or the endoscope connected at a previous time are detected, and settings of the group of the observed part including the ultrasound endoscope 2 can be edited giving priority.

When a new unit of the ultrasound endoscope 2 is to be introduced, a classification of an observed part (for example, urinary organ) can be added to the new unit of the ultrasound endoscope 2 together with information about the ultrasound endoscope 2. Furthermore, on an edit screen of settings, a classification of an observed part can be displayed on the display device 4.

When settings are edited, a scanning method (electronic or mechanical) of the connected ultrasound endoscope 2 may be detected. With this, editing is possible only for the detected scanning method.

When operator settings are written in an external medium (for example, a universal serial bus (USB) flash memory, or the like) from the main unit, information about the ultrasound endoscope 2 related to the settings is additionally written together with information of a date and a time of writing. When incorporating settings in from an external medium, searching can be performed based on information on a date and a time, an associated scope, and the like, and then the settings can be incorporated in.

When incorporating settings of the ultrasound endoscope 2, the type of which is different from the connected ultrasound endoscope 2, a setting item with significant deviation or an item, a setting range of which is different among items that can be set by the operator is substituted by an approximate value, or by a recommended setting value of the connected ultrasound endoscope 2.

According to the present disclosure, it is possible to implement an ultrasonic observation device, an ultrasonic diagnostic system, an operating method of an ultrasonic observation device, and an operating program of an ultrasonic observation device with which an intended operation is able to be performed without looking at a touch pad in the ultrasonic observation device to which an input device having the touch pad is connected.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation device comprising:
a processor configured to generate an ultrasound image based on a contact position of a contact of a contact object on a touch pad and based on an ultrasonic signal received from an ultrasound transducer; and
a display configured to display the ultrasound image,
wherein the processor is configured to:
receive a signal indicating the contact position,
generate ultrasound image data based on the ultrasonic signal,
associate each coordinate of a first coordinate space demarcated by the touch pad with each coordinate of a second coordinate space demarcated by the ultrasound image data,
calculate a coordinate of a rotation indicator that is a coordinate of the second coordinate space corresponding to the contact position,
generate the ultrasound image in which the rotation indicator is superimposed on the ultrasound image data at the coordinate of the rotation indicator, and
generate the ultrasound image in which the ultrasound image and the rotation indicator are rotated about a rotation reference as a center point when the contact position is changed; and
wherein the rotation reference is displayed on a portion of the ultrasound image displayed on the display, and wherein the portion of the displayed ultrasound image corresponds to a center of the ultrasound transducer.

2. The ultrasonic observation device according to claim 1, wherein the processor is configured to generate the ultrasound image in which the rotation indicator is removed at any one of timings after a first predetermined time has passed since a start of the contact to the touch pad, when the contact to the touch pad is ended, and after a second predetermined time has passed since an end of the contact.

3. The ultrasonic observation device according to claim 1, wherein the processor is configured to perform coordinate conversion such that the coordinate of the first coordinate space and the coordinate of the second coordinate space correspond with each other.

4. The ultrasonic observation device according to claim 1, wherein the processor is configured to:
associate the first coordinate space with the second coordinate space within an operation region of the touch pad;
assign a third coordinate space around the second coordinate space, the third coordinate space being a virtual region where the second coordinate space is expanded; and
associate each coordinate of the third coordinate space with each coordinate of the first coordinate space.

5. The ultrasonic observation device according to claim 1, wherein the rotation indicator includes at least one of a straight line extending from the rotation reference to the center point, a circle including the contact position, and an arrow that indicates a rotation direction according to the contact position.

6. The ultrasonic observation device according to claim 5, wherein the rotation indicator is either one of the straight line extending from the rotation reference to the center point, and the arrow that indicates the rotation direction according to the contact position.

7. The ultrasonic observation device according to claim 1, wherein when the contact position is changed from a first position to a second position, the processor is configured to generate the ultrasound image in which the ultrasound image and the rotation indicator are rotated about the center point based on an angle formed by the first position, the rotation reference and the second position.

8. The ultrasonic observation device according to claim 1, further comprising the touch pad, wherein the touch pad is provided separately from the display.

9. The ultrasonic observation device according to claim 1, further comprising an ultrasound endoscope including the ultrasound transducer configured to transmit an ultrasonic wave to an object to be observed and receive a reflected ultrasonic wave reflected by the object, and transmit the ultrasonic signal to the ultrasonic observation device.

10. The ultrasonic observation device according to claim 1, wherein the coordinate of the rotation indicator is a coordinate of a center of the contact position.

11. The ultrasonic observation device according to claim 1, wherein the processor is configured to move a position of the rotation reference such that the position of the rotation reference matches the center of the ultrasound transducer when the center of the ultrasound transducer moves.

12. The ultrasonic observation device according to claim 1, wherein the processor is configured to:
generate the ultrasound image in which the rotation indicator is removed at any one of timings after a first predetermined time has passed since a start of the contact to the touch pad, when the contact to the touch pad is ended, and after a second predetermined time has passed since an end of the contact,
wherein the coordinate of the rotation indicator is a coordinate of a center of the contact position, and
the rotation indicator includes at least one of a straight line extending from the rotation reference to the center point, a circle including the contact position, and an arrow that indicates a rotation direction according to the contact position.

13. The ultrasonic observation device according to claim 1, further comprising an input device including the touch pad configured to detect the contact and the contact position of the contact object.

14. A method of operating an ultrasonic observation device, the method comprising:
detecting a contact to a touch pad and a contact position of a contact object;
generating an ultrasound image based on the contact position and based on an ultrasonic signal received from an ultrasound transducer; and
displaying the ultrasound image, wherein
the generating includes:
generating ultrasound image data based on the ultrasonic signal,
associating each coordinate of a first coordinate space demarcated by the touch pad with each coordinate of a second coordinate space demarcated by the ultrasound image data,
calculating a coordinate of a rotation indicator that is a coordinate of the second coordinate space corresponding to the contact position,
generating the ultrasound image in which the rotation indicator is superimposed on the ultrasound image data at the coordinate of the rotation indicator, and
generating the ultrasound image in which the ultrasound image and the rotation indicator are rotated about a rotation reference as a center point when the contact position is changed;
wherein the rotation reference is displayed on a portion of the ultrasound image displayed on a display, and
wherein the portion of the displayed ultrasound image corresponds to a center of the ultrasound transducer.

15. A non-transitory computer-readable recording medium on which an executable program is recorded, the executable program causing a processor of an ultrasonic observation device to execute:
detecting a contact to a touch pad and a contact position of a contact object;
generating an ultrasound image based on the contact position and based on an ultrasonic signal received from an ultrasound transducer; and
displaying the ultrasound image, wherein
the generating includes:
generating ultrasound image data based on the ultrasonic signal,
associating each coordinate of a first coordinate space demarcated by the touch pad with each coordinate of a second coordinate space demarcated by the ultrasound image data,
calculating a coordinate of a rotation indicator that is a coordinate of the second coordinate space corresponding to the contact position,
generating the ultrasound image in which the rotation indicator is superimposed on the ultrasound image data at the coordinate of the rotation indicator, and
generating the ultrasound image in which the ultrasound image and the rotation indicator are rotated about a rotation reference as a center point when the contact position is changed;
wherein the rotation reference is displayed on a portion of the ultrasound image displayed on a display, and wherein the portion of the displayed ultrasound image corresponds to a center of the ultrasound transducer.

* * * * *